(12) United States Patent  
Marino

(10) Patent No.: US 8,211,013 B2  
(45) Date of Patent: Jul. 3, 2012

(54) SPECULUM

(75) Inventor: James Marino, La Jolla, CA (US)

(73) Assignee: Trinty Orthopedics, LLC., San Diego, CA (US)

( * ) Notice: Subject to any disclaimer, the term of this patent is extended or adjusted under 35 U.S.C. 154(b) by 1316 days.

(21) Appl. No.: 11/904,308

(22) Filed: Sep. 25, 2007

(65) Prior Publication Data

US 2008/0091081 A1    Apr. 17, 2008

Related U.S. Application Data

(60) Provisional application No. 60/847,481, filed on Sep. 26, 2006.

(51) Int. Cl.  
*A61B 1/32* (2006.01)

(52) U.S. Cl. .................................... 600/219

(58) Field of Classification Search .............. 600/201, 600/210, 214–215, 218–220, 226, 235, 184, 600/196, 197, 200; 606/205–208  
See application file for complete search history.

(56) References Cited

U.S. PATENT DOCUMENTS

| | | | |
|---|---|---|---|
| 4,502,468 A * | 3/1985 | Burgin | ........................... 600/212 |
| 5,797,959 A | 8/1998 | Castro et al. | |
| 5,891,147 A | 4/1999 | Moskovitz | |
| 5,916,150 A | 6/1999 | Sillman | |
| 6,450,952 B1 | 9/2002 | Rioux et al. | |
| 6,592,587 B1 | 7/2003 | Roger | |

* cited by examiner

*Primary Examiner* — Anu Ramana  
(74) *Attorney, Agent, or Firm* — Fred C. Hernandez; Mintz, Levin, Cohn, Ferris, Glovsky and Popeo, P.C.

(57) ABSTRACT

Disclosed are devices and methods for accessing and channeling through biological tissue. One embodiment is a bone access tool including a handle assembly and speculum assembly coupled to the handle assembly. The handle assembly has first and second portions that are movable relative to one another. The speculum assembly has first and second speculum members movably positioned relative to one another. The speculum members define an internal shaft arranged about a central axis and a tapered shape when positioned adjacent one another. The tapered shape gradually reduces in size from a proximal rim to a distal edge of the speculum assembly. The speculum assembly also has at least one rib extending outwardly from each of the first and second speculum members, the rib having an upper surface and an inclined lower surface. Actuation of the handle assembly causes the first speculum member and second speculum member to spread apart from one another about the central axis so as to retract anatomical tissue and widen a size of the internal shaft for deploying a tool into the internal shaft between the speculum members.

21 Claims, 11 Drawing Sheets ized locations where the speculum cap 150 can be used

SPECULUM

REFERENCE TO PRIORITY DOCUMENT

This application claims priority of U.S. Provisional Patent Application Ser. No. 60/847,481 filed Sep. 26, 2006. Priority of the aforementioned filing date is hereby claimed and the disclosure of the Provisional Patent Application is hereby incorporated by reference in its entirety.

BACKGROUND

The present disclosure relates to a system for accessing and channeling tissue, such as bone tissue.

It is often necessary to access regions of anatomical tissue such as for insertion of a tool for treating or sampling the tissue. For example, a tool is sometimes used to obtain a core sample of biological material such as to diagnose defects or ailments. To obtain a sample, an instrument me be used to remove a portion or a "core sample" from surrounding biological material. In order for the tool to provide a proper approach to the relevant tissue, there is a need for systems and methods that facilitate in gaining access to tissue.

SUMMARY

There is a need for improved devices and methods for accessing and channeling through biological tissue.

In one embodiment, disclosed is a bone access tool including a handle assembly having a first portion and a second portion that are movable relative to one another; a speculum assembly coupled to the handle assembly, the speculum assembly having a first speculum member; a second speculum member movably positioned relative to the first speculum member, wherein the first and second speculum members define an internal shaft therebetween arranged about a central axis, and the first and second speculum members define a tapered shape when positioned adjacent one another, the tapered shape gradually reduces in size from a proximal rim to a distal edge of the speculum assembly; and at least one rib extending outwardly from each of the first and second speculum members, the rib having an upper surface and an inclined lower surface. Actuation of the handle assembly causes the first speculum member and second speculum member to spread apart from one another about the central axis so as to retract anatomical tissue and widen a size of the internal shaft for deploying a tool into the internal shaft between the speculum members.

In an embodiment, disclosed is a method of accessing bone, including providing an access tool having a handle assembly coupled to a speculum assembly formed of two speculum members that collectively form a substantially conical shape with a pointed distal edge; navigating the access tool through anatomical tissue so that the pointed distal edge of the speculum assembly is located at a desired anatomical location; actuating the handle to cause the speculum members to separate from one another to retract anatomical tissue and to form a passageway between the speculum members; and positioning an elongated tool in the passageway and in contact with the anatomical location.

Other features and advantages will be apparent from the following description of various embodiments, which illustrate, by way of example, the principles of the disclosed devices and methods.

DETAILED DESCRIPTION

Figure 1:
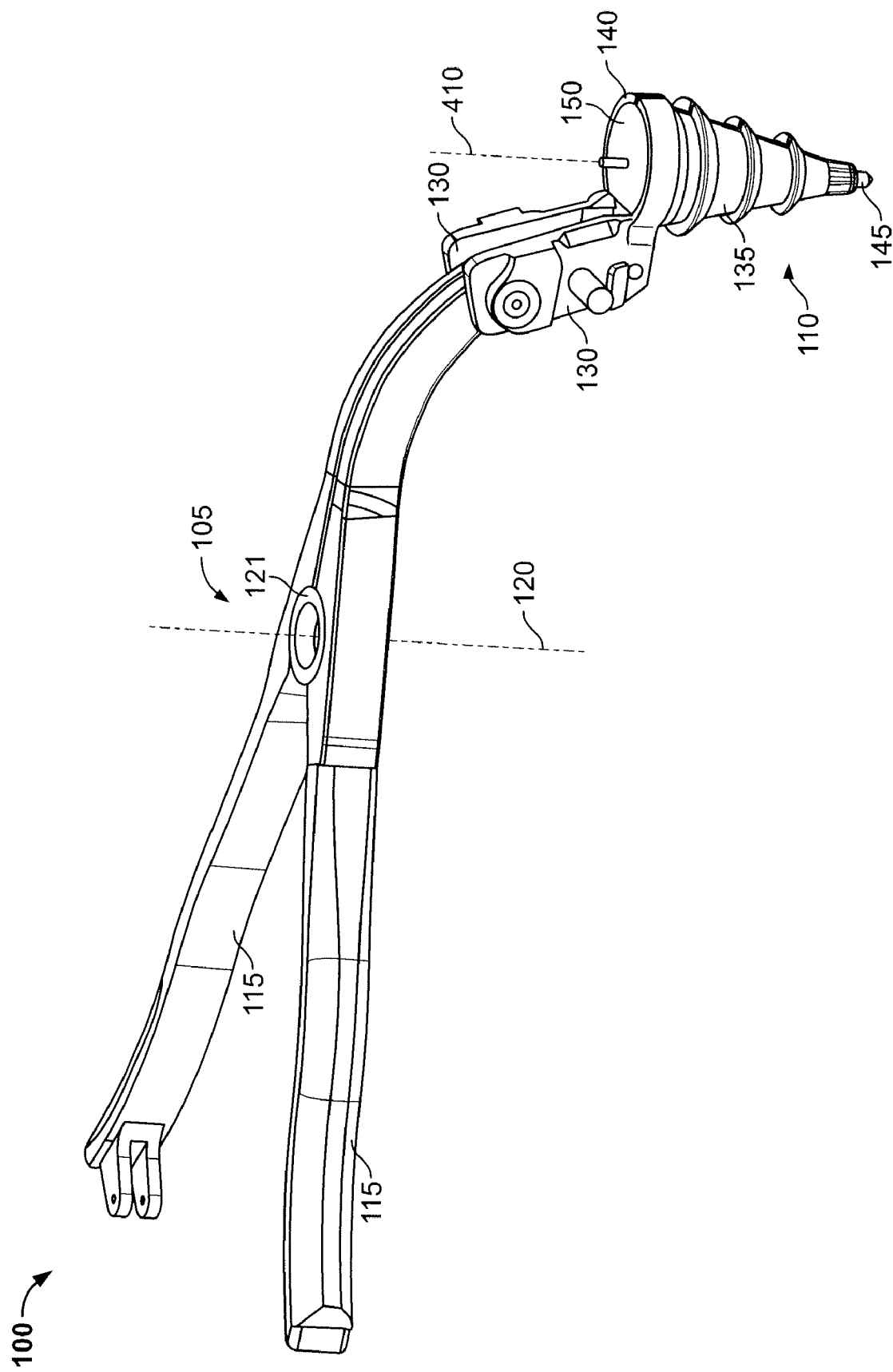
FIG. 1 shows a perspective view of a tissue access and channel formation system.

FIG. 1 shows a perspective view of a tissue access and channel formation system 100. The system 100 includes a handle assembly 105 and a conical speculum assembly 110 attached to the handle assembly 105. The handle assembly 105 includes a pair of arms 115 that are pivotably attached to one another about a pivot axis 120. The arms 115 pivot about a circular pivot member 121 such as when a user actuates the handle assembly 105. The pivot member 121 can be ratcheted such that movement of the arms 115 relative to one another is controlled by a ratchet mechanism. The arms 115 are shaped and contoured such that the arms extend away from one another at the pivot member 121 and are positioned adjacent one another along a region adjacent the speculum assembly 110.

The speculum assembly 110 is pivotably attached to the handle assembly 105 via a pair of speculum couplers 130. The speculum assembly 110 includes a pair of semi-conical speculum members 135 that collectively form a conical shape when positioned adjacent one another, as shown in FIG. 1. The conical speculum assembly 110 is symmetric about a central axis 410. In the illustrated embodiment, the speculum assembly 110 is widest at a proximal rim 140 and gradually tapers in diameter toward a distal edge 145 that is pointed. The conical shape facilitates soft tissue penetration and dilation of a surgical access envelope during use of the device, as described below. It should be appreciated that the shape of the speculum assembly 110 can vary from the conical shape and can have other shapes that facilitate soft tissue penetration and dilation of a surgical access envelope. For example, the speculum assembly 110 can have a shape that generally tapers moving in the distal direction with the taper being linear or curvilinear.

A speculum cap 150 is removably positioned on the speculum assembly 110 at the proximal rim 140. The speculum cap 150 forms a flat or generally flat upper surface. The upper surface of the speculum cap 150 provides a location where a striking tool, such as hammer, mallet, or the like, can be used to strike the speculum assembly 110 and provide a downward or distal force to the assembly. This can be desirable when driving the distal edge of the speculum assembly 110 into tissue. The speculum cap 150 can be coupled to the speculum assembly 110 in various manners. For example, the speculum cap 150 can fit within a seat in the upper rim 140 of the speculum assembly 110 or it can hinged or can have locked detent engagement feature with the speculum assembly 110. The speculum cap 150 can be removed from the speculum assembly 110 to expose an internal speculum shaft 320 (FIG. 3) positioned inside the speculum assembly 110 between the speculum members 135, as described in detail below.

The speculum cap 150 can include an opening or aperture that communicates with the internal speculum shaft 320. The opening provides a passageway through which a guide pin or guide wire can be inserted. In this regard, the opening desirably has a shape or contour that facilitates insertion of the guide wire into the opening. For example, the opening can be at least partially conical or can have a countersunk feature that facilitates "blind" introduction of the guide wire into the opening.

Figure 2:
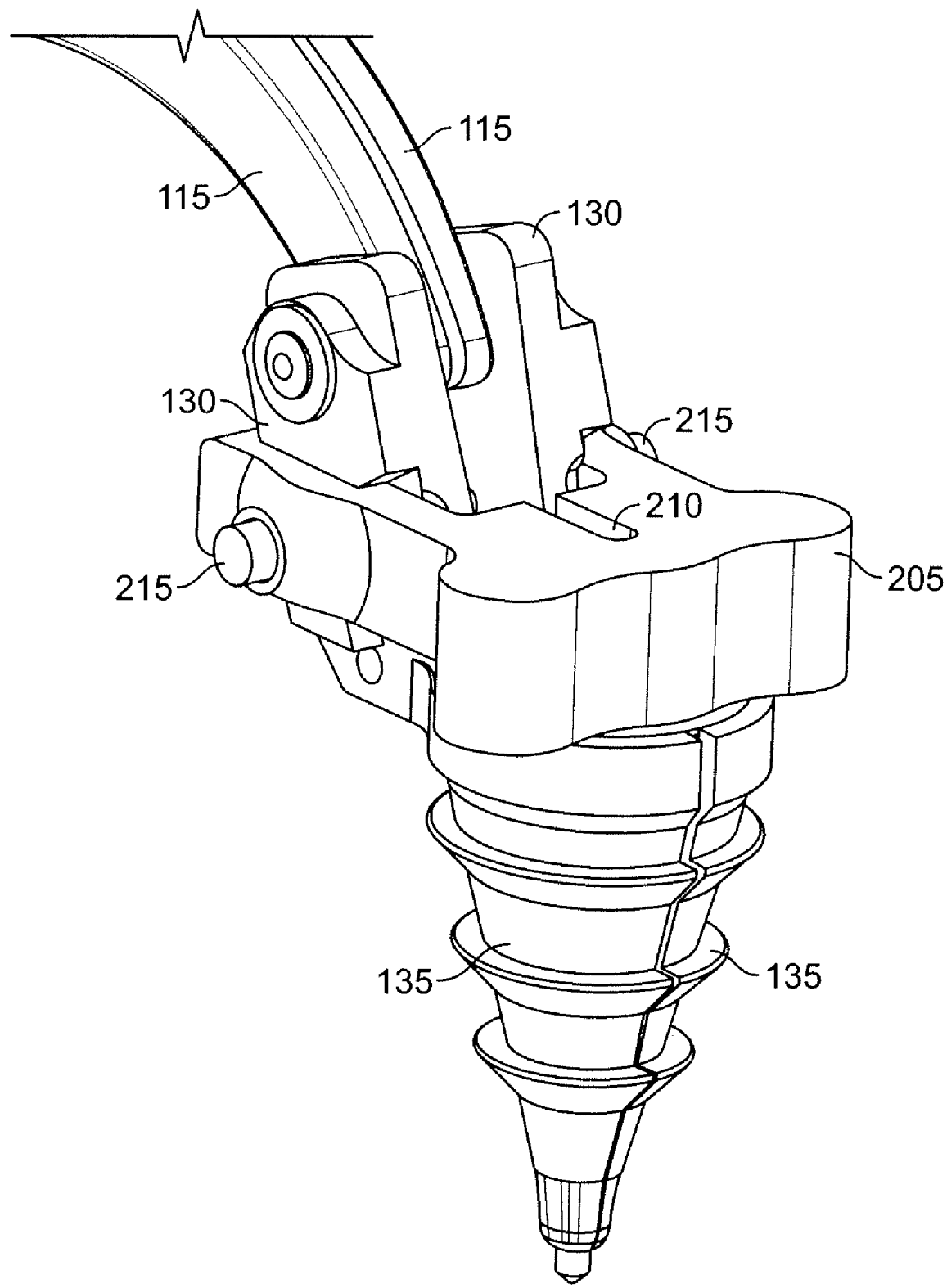
FIG. 2 shows an enlarged view of a speculum assembly of the system with a locking member mounted onto the speculum assembly.

FIG. 2 shows an enlarged view of the speculum assembly 110 with a locking member 205 mounted onto the speculum assembly 110. The locking member 205 is a clamp-like member that maintains the speculum members 135 in a fixed spatial relationship. For example, the locking member 205 can hold the two arms 115 together to prevent them from spreading apart and thereby prevent spreading of the speculum members 135. In this regard, the locking member 205 includes a pair of flanges that are positioned on opposite sides of the arms 115 to oppose outward motion of the arms 115. Thus, when the locking member 205 is mounted on the system, the arms 115 and the attached speculum members 135 are prevented from separating from one another. The locking member 205 is removably mounted on the speculum assembly 110. A pair of locking member pins 215 removably mate with the locking member 205 and the speculum coupler 130. The locking member pins 215 can be slidably uncoupled from the speculum coupler 130 to release the locking member 205 from the speculum assembly 110.

With reference still to FIG. 2, a guide slot 210 extends through the locking member 205. The slot 210 communicates with the internal speculum shaft 320 (FIG. 4) located between the speculum members 135. The slot 210 is aligned or substantially aligned with the central axis 410 of the speculum assembly 110. A guide pin or guide wire can be positioned through the slot 210 and the internal speculum shaft 320 to assist in navigating through tissue during use of the system, as described more fully below.

Figure 3:
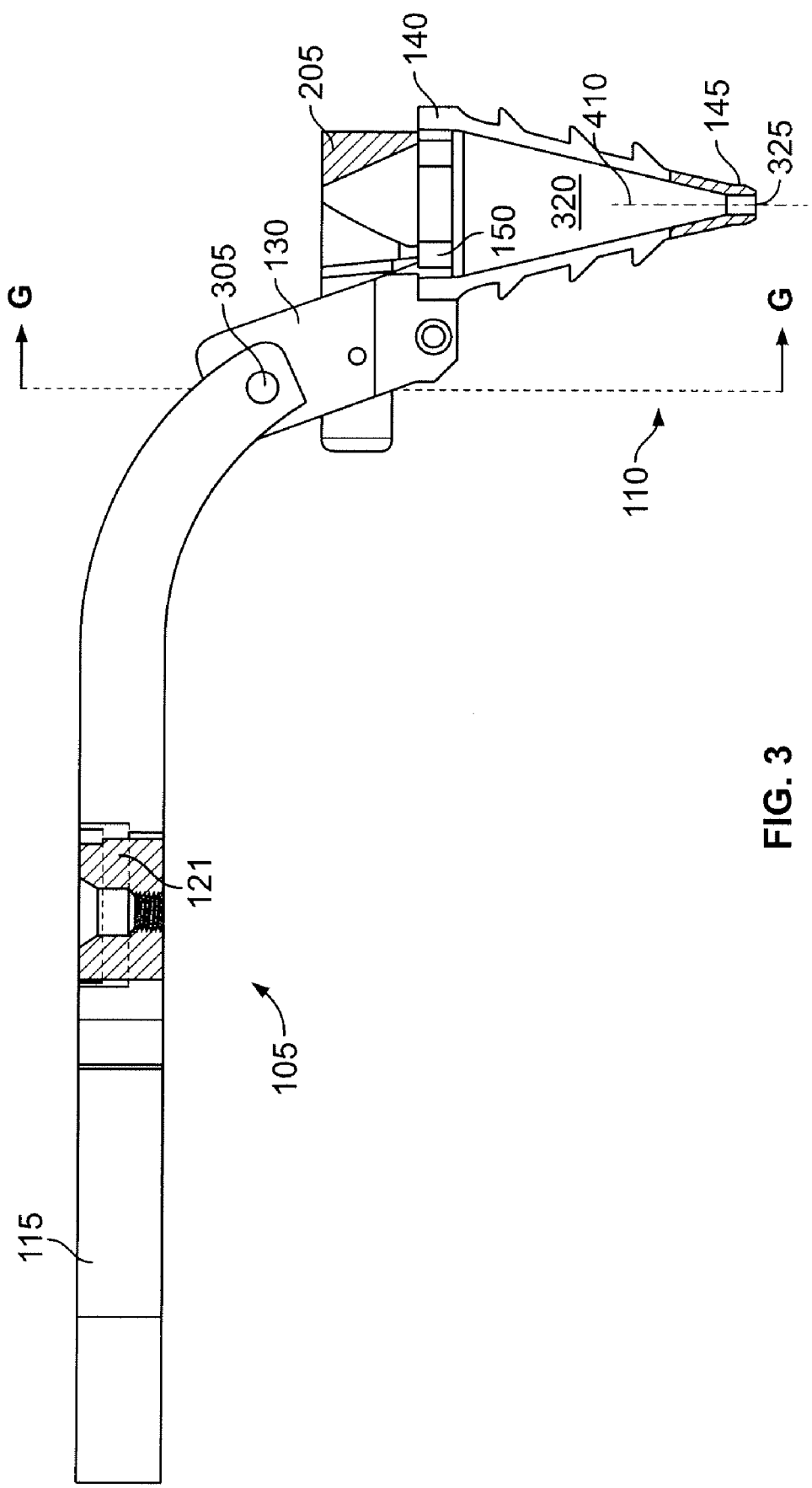
FIG. 3 shows a side view of the system in cross-section.

FIG. 3 shows a side view of the system in cross-section. The opposite side view is a mirror image of the side view shown in FIG. 3. Each arm 115 extends along a generally longitudinal axis that intersects the central axis 410. The end regions of the arms 115 curve downwardly toward the speculum assembly 110. Each arm 115 is pivotably attached to a respective speculum coupler 130 via a pivot pin 305. Each pivot pin 305 defines a pivot axis about which the arm 115 can pivot relative to the speculum assembly. Thus, the handle assembly 105 is hinged relative to the speculum assembly 110. As mentioned, the arms 115 are pivotably attached to one another via the circular pivot member 121, which can be secured to the arms 115 via a pivot screw that defines a pivot axis about which the arms 115 pivot relative to one another.

FIG. 3 shows the internal speculum shaft 320 that is positioned inside the speculum assembly 110. The speculum shaft 320 has a conical shape with a gradually decreasing diameter that is largest at the proximal rim 140 of the speculum assembly 110. The speculum shaft 320 gradually tapers in diameter moving toward the distal edge 145 of the speculum assembly 110. A distal opening 325 is at the distal edge of the speculum assembly 110 such that the speculum shaft 320 is open at the distal edge 145. The opening 325 aligns or generally aligns along a common axis 410 with the internal speculum shaft 320, the opening in the speculum cap 150, and the guide slot 210 (FIG. 2) of the locking member 205. This permits a guide wire or guide pin to be inserted through the entire speculum assembly 110 and locking member 205 to assist in navigation of the system through tissue during use.

Figure 4:
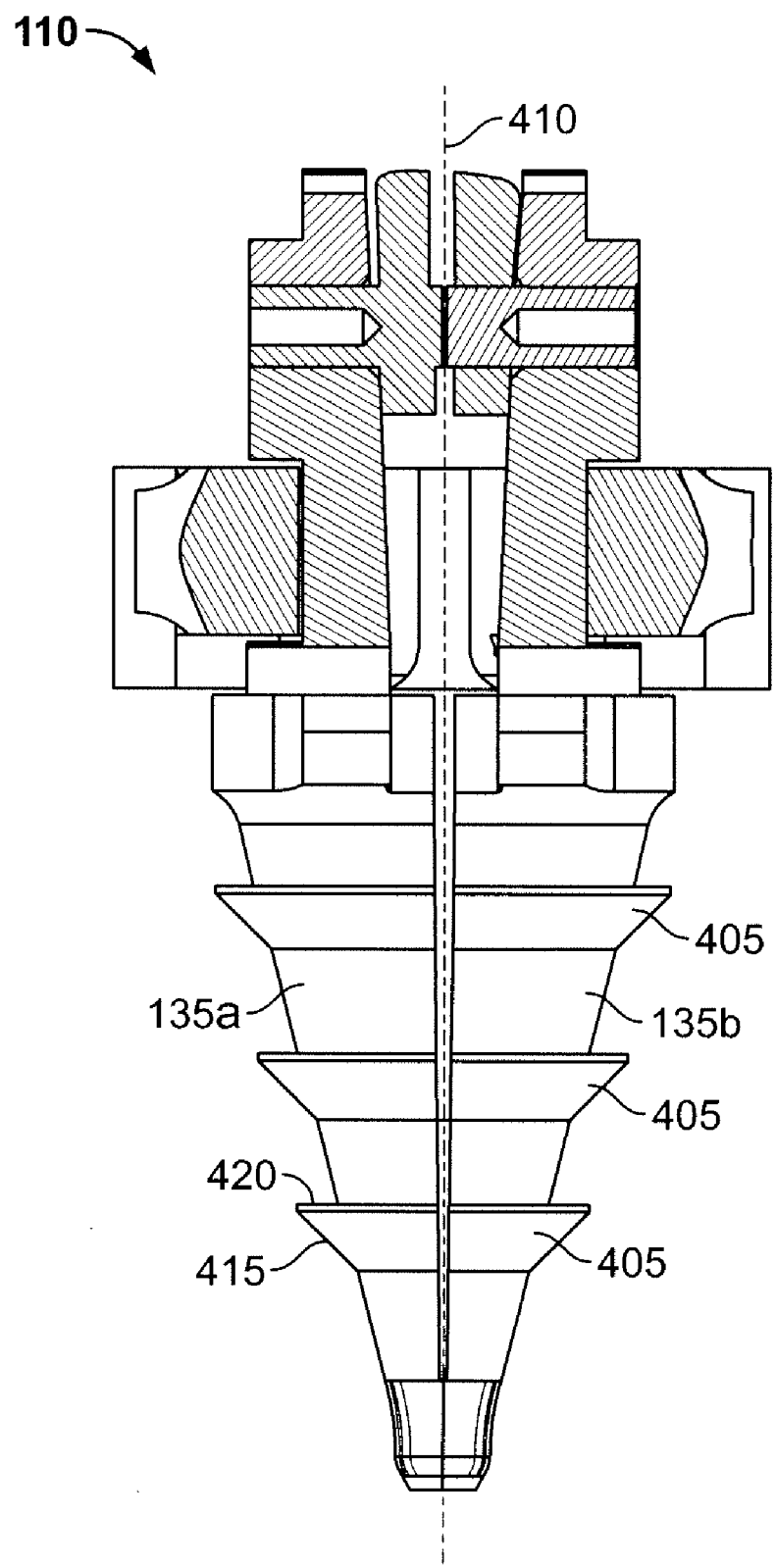
FIG. 4 shows a side view of the speculum assembly along line G-G of FIG. 3.

FIG. 4 shows a side view of the speculum assembly 110 along line G-G of FIG. 3. As discussed, the speculum assembly 110 includes a pair of speculum members 135 that are semi-conical in shape. The speculum members 135 are referred to herein individually as speculum member 135a and speculum member 135b. The speculum members 135 collectively form a conically-shaped speculum when positioned adjacent one another as in FIG. 4. The speculum members 135 have walls that meet along a central plane that intersects with the central axis 410 of the conical speculum assembly 110. The central plane is perpendicular to a plane defined by FIG. 4. The speculum members 135 can mate with one another along the adjacent walls such as in an interdigitating manner in order to stabilize the speculum members 135 relative to one another during use of the system 100.

With reference still to FIG. 4, one or more protruding flanges or ribs 405 are interspersed along the speculum members from the proximal rim 140 to the distal edge 145. The illustrated embodiment includes three annular ribs 405 although it should be appreciated that additional ribs 405 or less ribs 405 can be used. The ribs 405 extend radially outward relative to the central axis 410 of the speculum assembly 110. Each rib 405 has a bottom surface 415 and an upper surface 420. In the illustrated embodiment, the bottom surface 415 of each rib 405 is upwardly sloped. The upper surface 420 of each rib 405 is horizontal. The upwardly sloped bottom surfaces 415 assist in displacement of tissue upon insertion of the system 100 into tissue and also assist in rotation of the speculum. It should be appreciated that the ribs 405 can have other shapes.

Figure 5A:
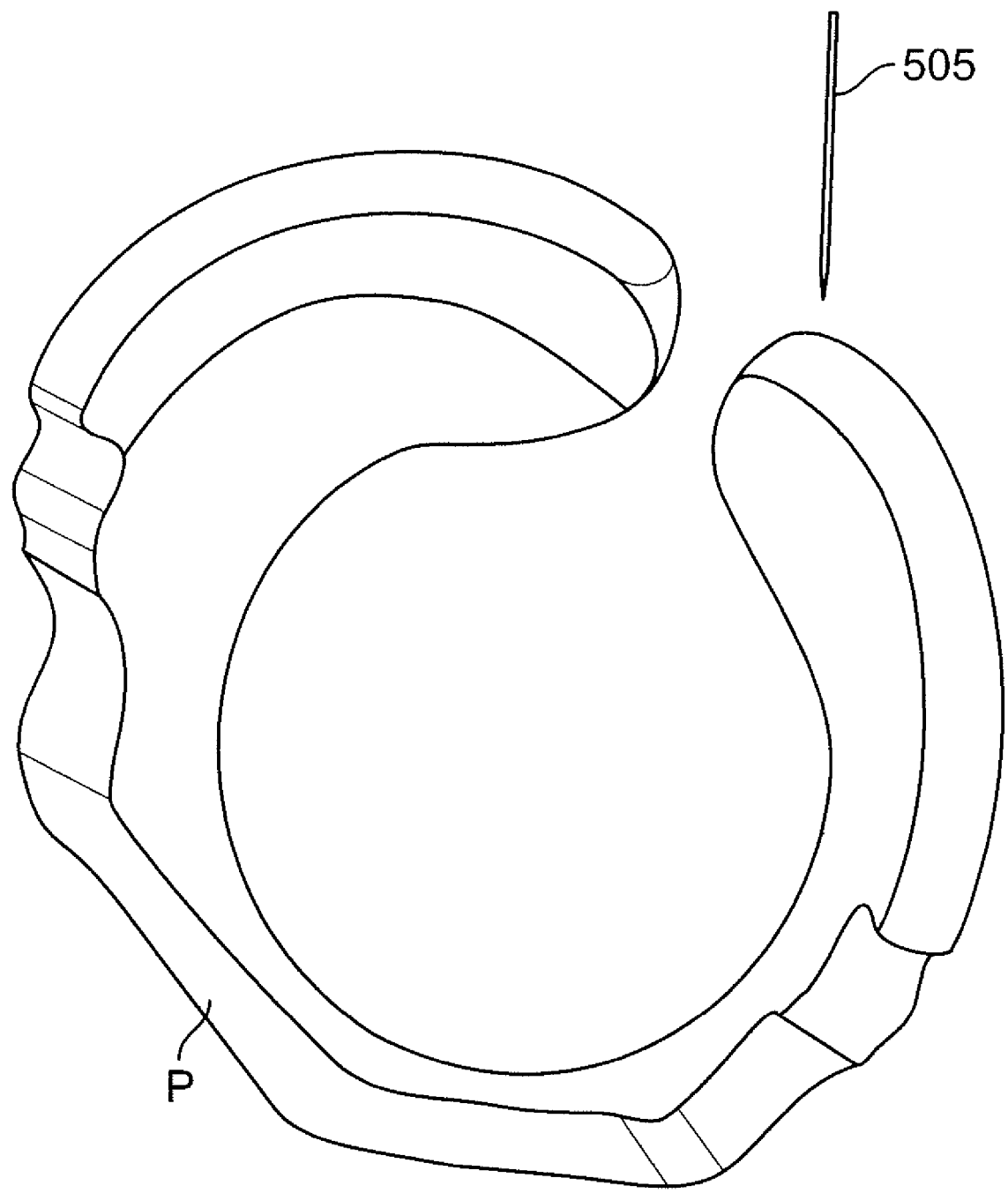
FIG. 5A shows a guide wire or guide pin to be inserted into a region of the iliac crest of the pelvis.

FIGS. 5A-5G are diagrams of an exemplary tissue access and channel formation method that uses the system shown in FIG. 1. In an exemplary embodiment, the device and method are used within or in the region of a person's vertebral bones. For example, the device and method can be employed to gain access to a mammalian patient's pelvis P, such as in the region of the iliac crest. With reference to FIG. 5A, a guide wire or guide pin 505 is inserted into a region of the iliac crest. One or more guidance systems can be used to navigate the guide pin 505 to a desired location of the iliac crest. For clarity of illustration, FIGS. 5A-5G schematically represent the pelvis P and do not include anatomical structures or tissue that are present around the pelvis P.

Figure 5B:
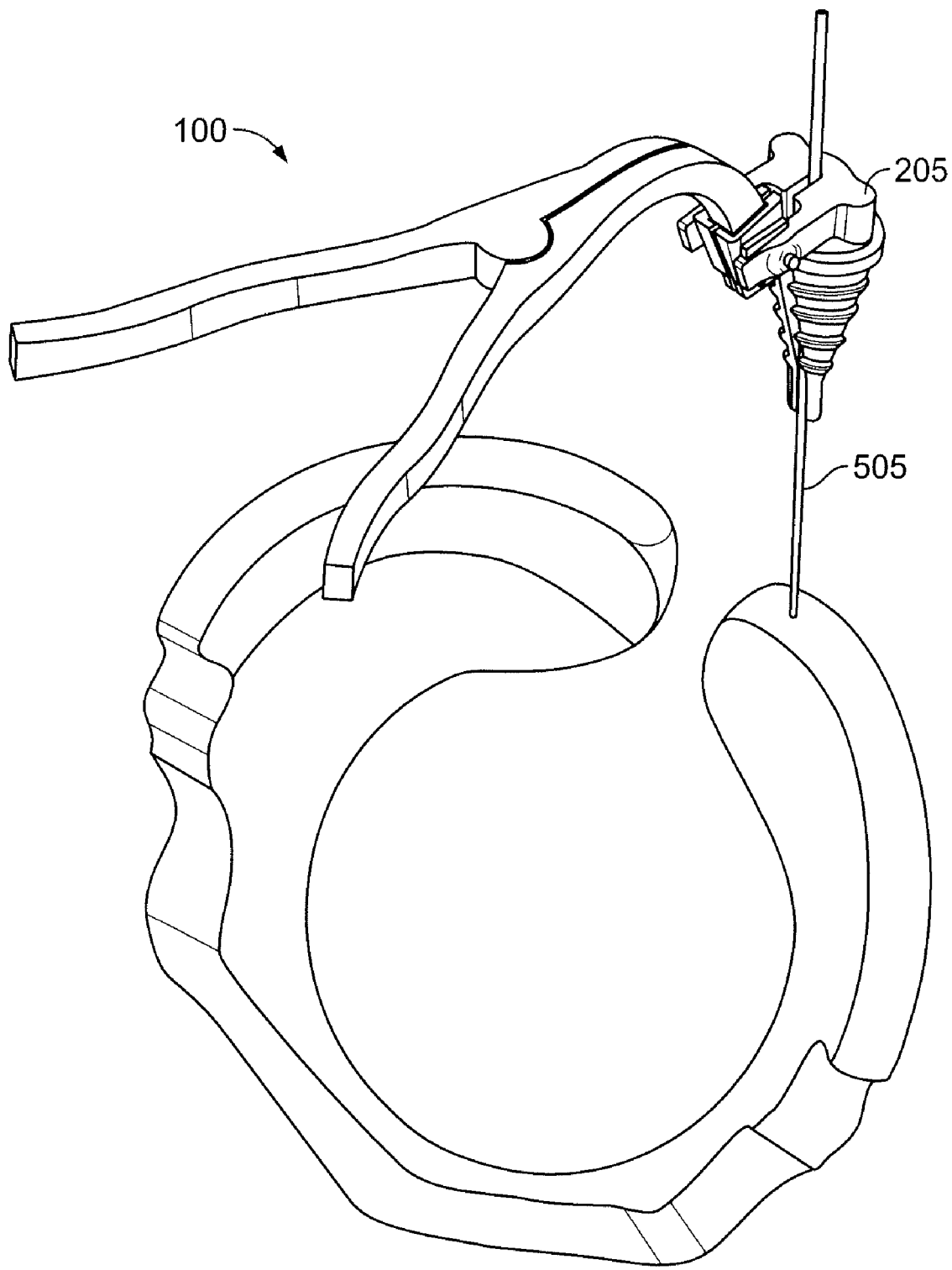
FIG. 5B shows the system being guided along the inserted guide pin toward the iliac crest.

The tissue access system 100 is then placed over the guide pin 505 and navigated to a desired location of the iliac crest. In this regard, an incision may be made in surrounding tissue and the conical speculum assembly 110 inserted through the incision. The handle assembly 105 can remain outside of the patient's skin. As discussed, the locking member 205 has a guide slot 210 that communicates with the internal speculum shaft 320. The tissue access system 100 is guided to the desired iliac crest location by sliding the guide slot 210 and the internal speculum shaft 320 along the guide pin 505. FIG. 5B shows the system 100 being guided along the guide pin 505 toward the iliac crest.

Figure 5C:
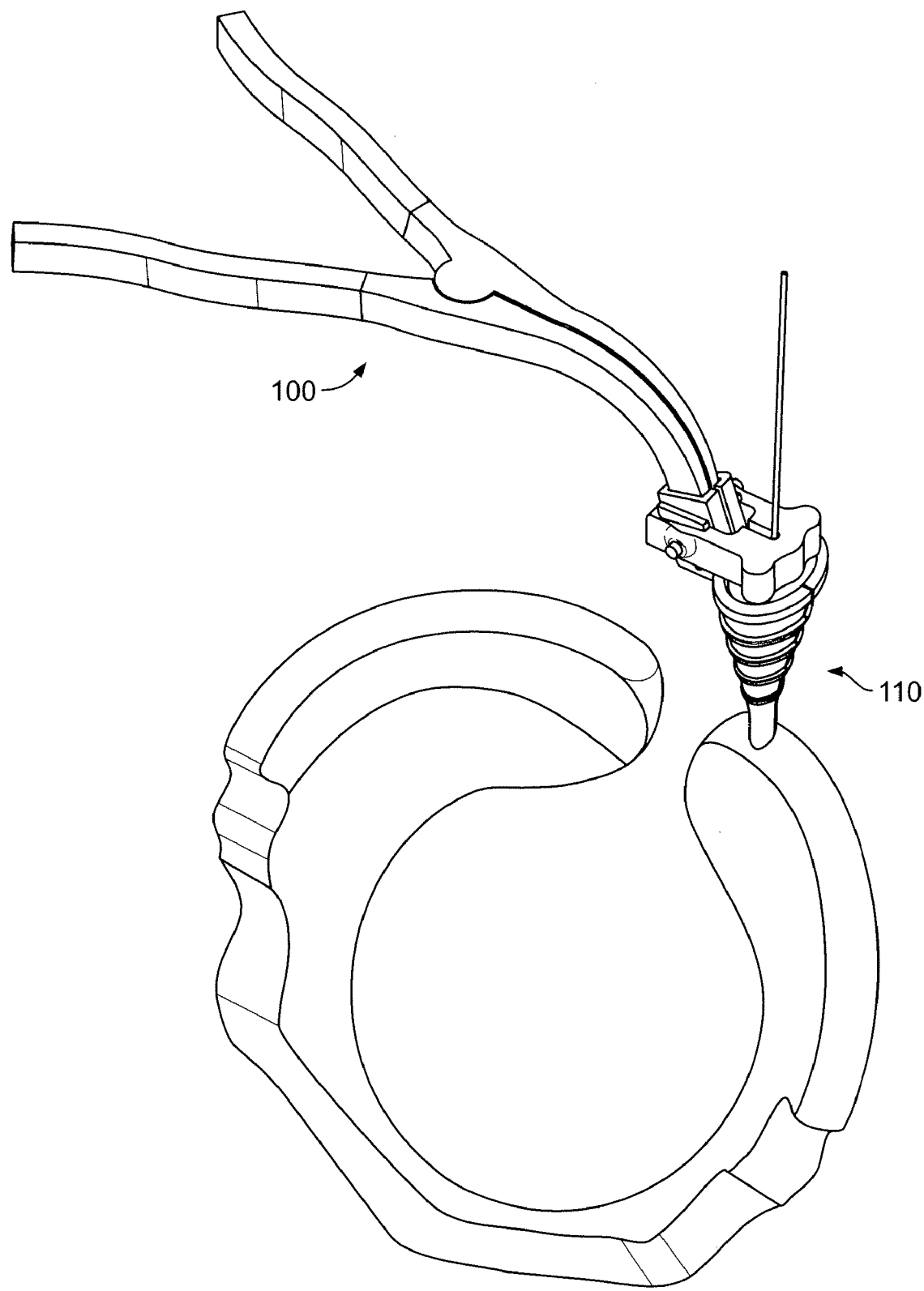
FIG. 5C shows the system with the speculum assembly in a possible desired orientation relative to the iliac crest.

The system 100 can advantageously be rotated in various manners as the system navigates through the tissue. For example, the handle assembly 105 and speculum assembly 110 can be rotated about the guide pin 505. The handle assembly 105 can also rotate relative to the speculum assembly 110 about the pivot pin 305 (FIG. 3). In this manner, the handle assembly 105 can be maneuvered to a desired orientation, such as to enhance the distraction, cut the fascia and tissue adjacent to the crest and correctly orient the speculum assembly 110. FIG. 5C shows the system 100 with the speculum assembly in a possible desired orientation relative to the iliac crest. The system 100 is positioned such that the distal edge of the speculum assembly 110 contacts the iliac crest. As mentioned, a hammer or mallet can be used to apply a force to the speculum assembly 110 for driving the speculum assembly 110 into tissue.

Figure 5D:
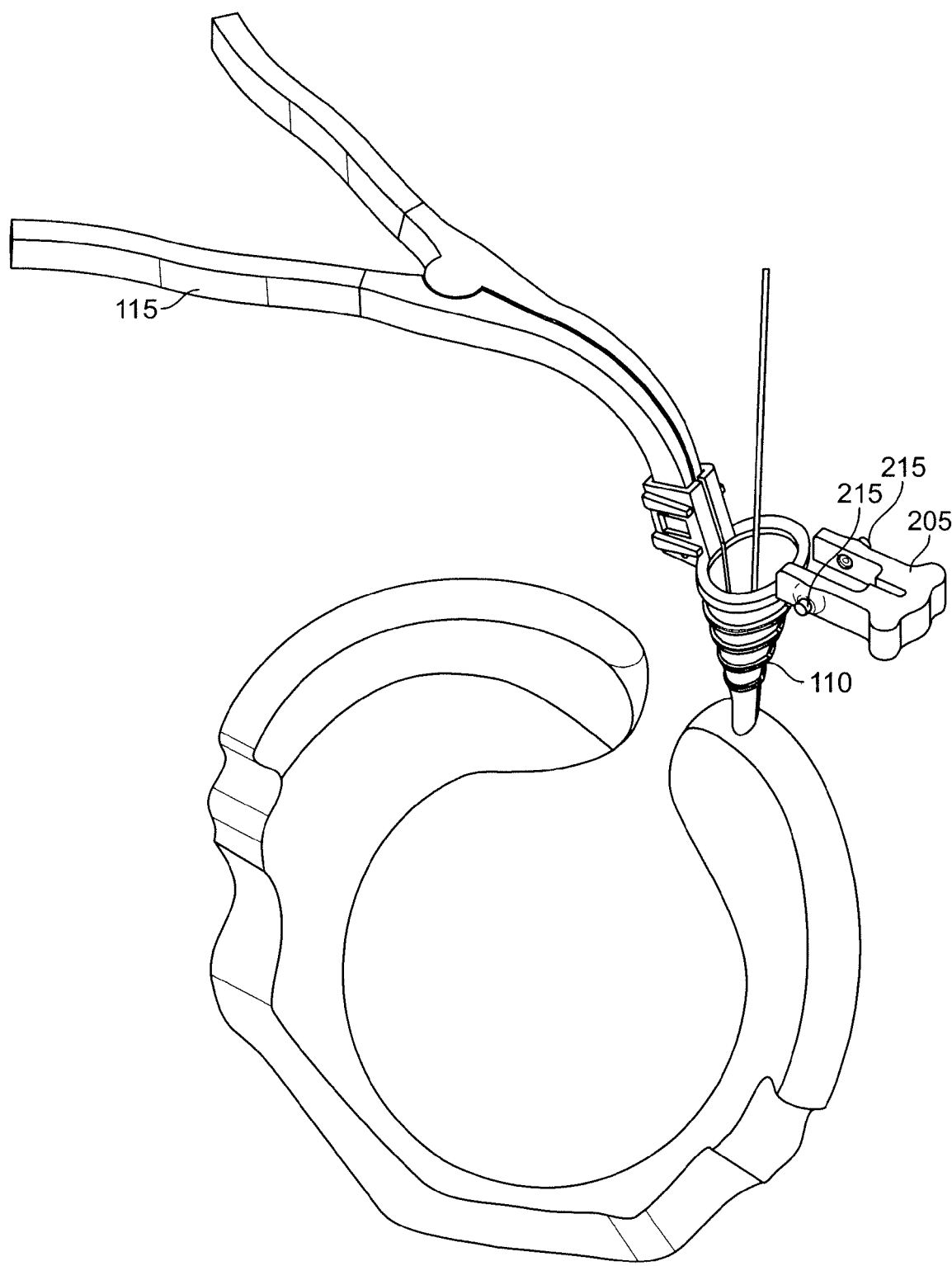
FIG. 5D shows a locking member removed from the speculum assembly.
Figure 5E:
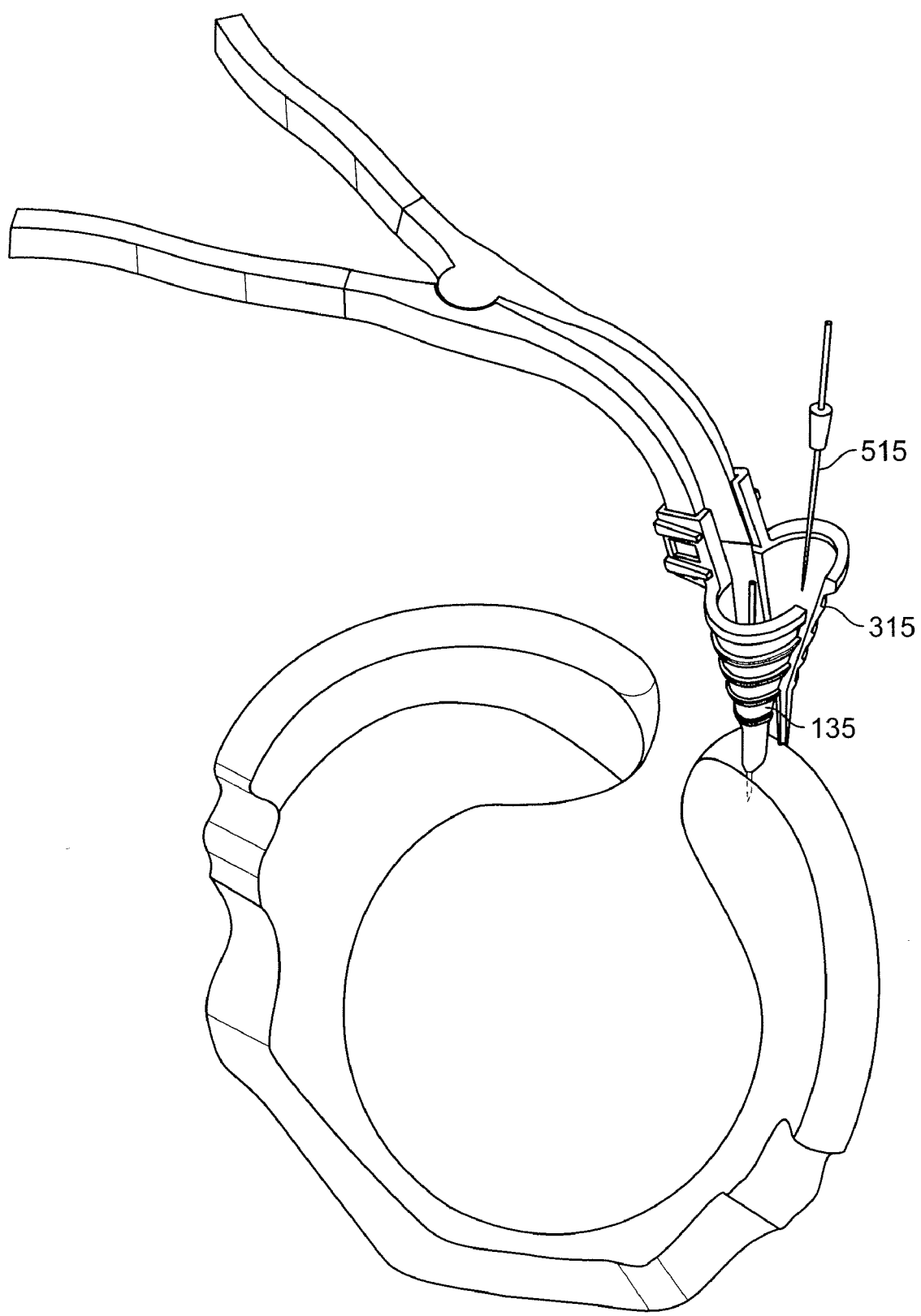
FIG. 5E shows the system with the speculum members displaced from one another to displace and expand surrounding tissue.

After the system 100 has been properly orientated, the physician may remove the locking member 205 from the speculum assembly 110. FIG. 5D shows the locking member 205 removed from the speculum assembly 110. As mentioned, the locking member pins 215 can be removed to release the locking member 205 from the system 100. With the locking member 205 removed, the speculum members 135 are free to be separated from one another. This is accomplished by the physician squeezing the arms 115 of the handle assembly 110 toward one another. This causes the distal regions of the arms 115 to pivot away from one another, thereby displacing the speculum members 135 relative to one another. FIG. 5E shows the system 100 with the speculum members 135 displaced from one another such that the speculum members 135 displace and expand surrounding tissue. During separation of the speculum members 135, the ribs 405 stabilize the speculum assembly 110 against the surrounding tissue. A passageway is thereby formed between the speculum members 135 wherein the passageway can be used to visualize the anatomy and/or deliver one or more tools to the iliac crest. In an embodiment, one or more anchor pins 515 can be inserted into the speculum members 135 to immobilize them in the displaced positions.

Figure 5F:
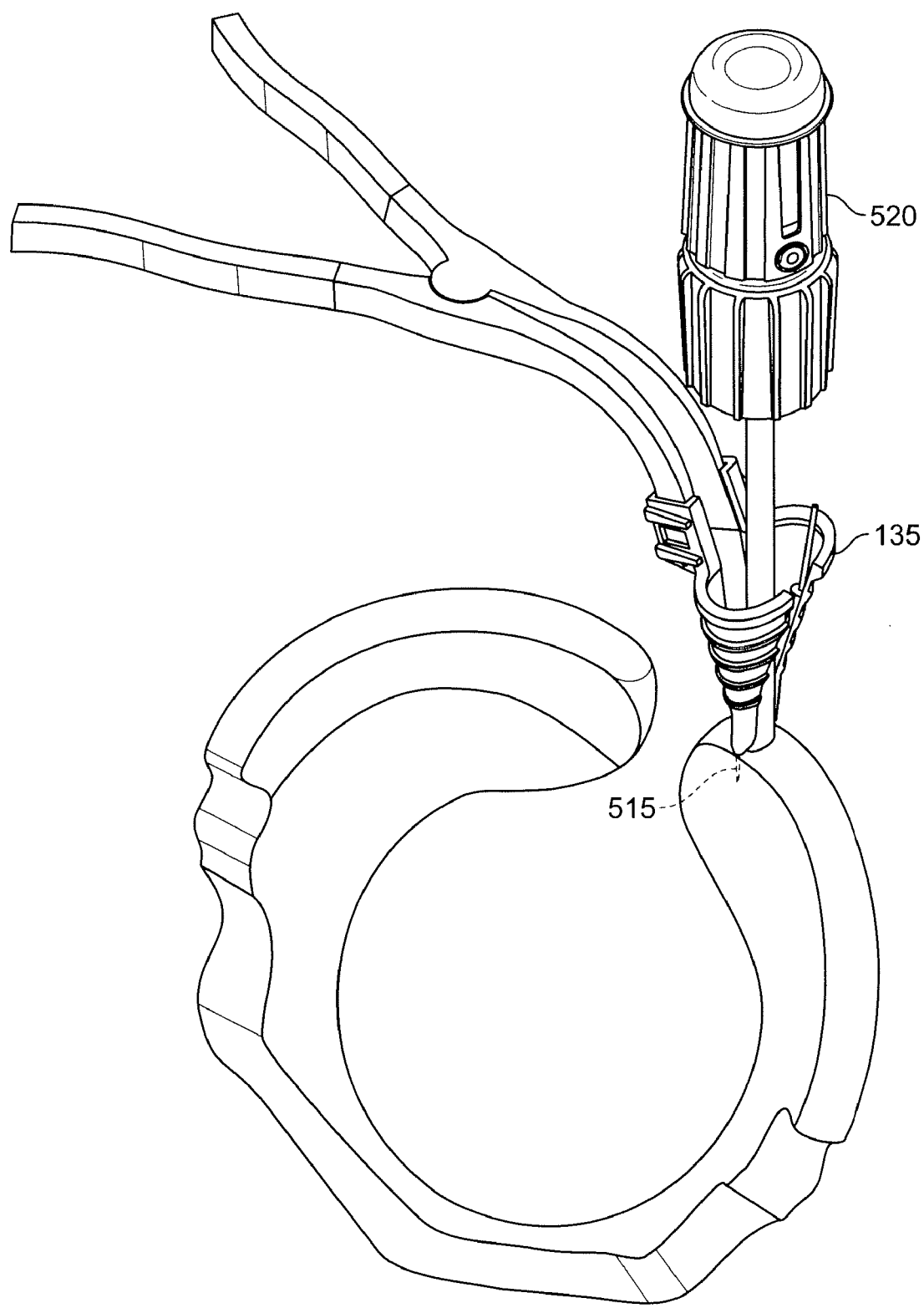
FIGS. 5F and 5G show the system with a coring tool positioned at least partially within the passageway between the speculum members.
Figure 5G:
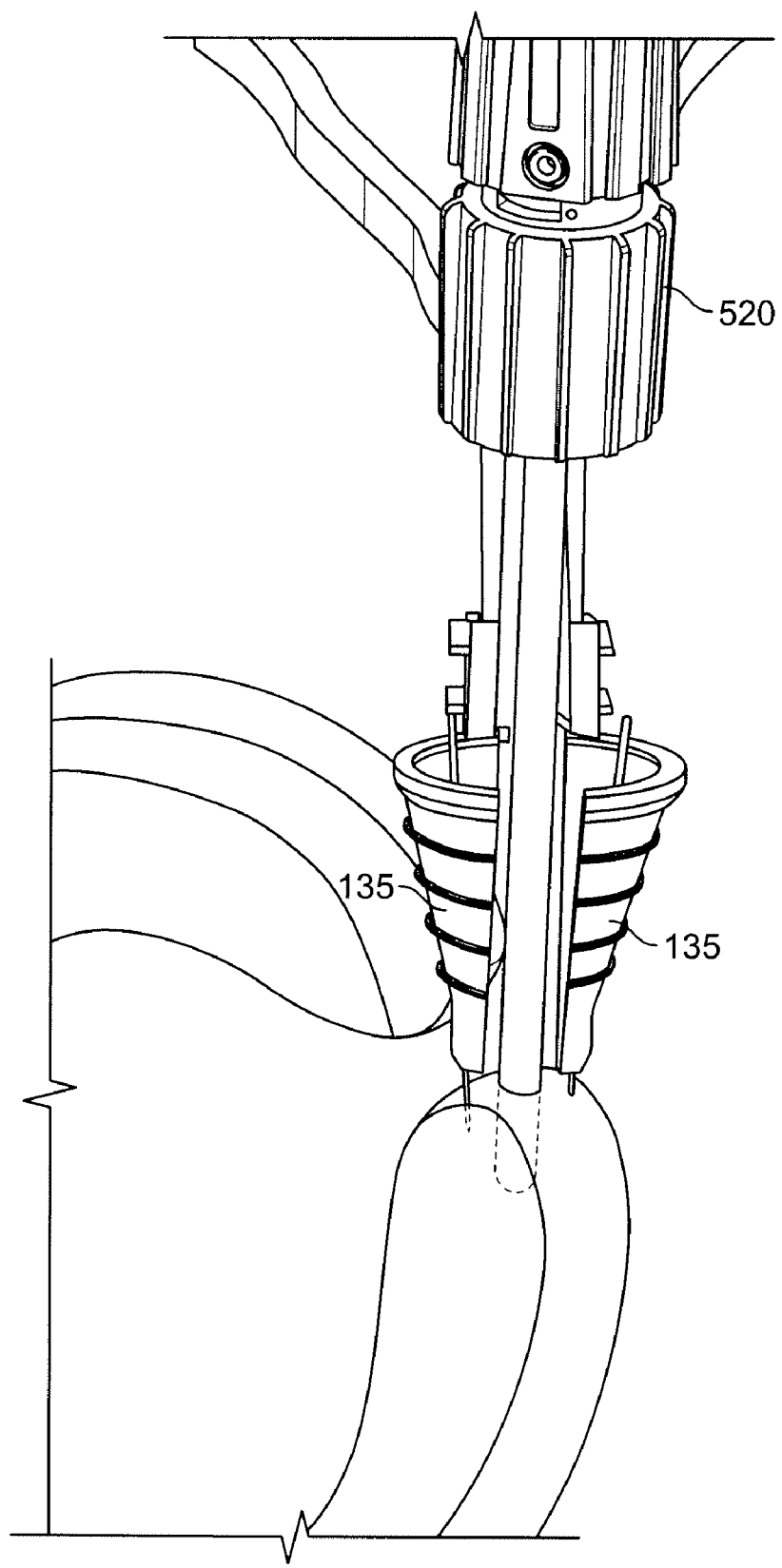

FIGS. 5F and 5G show the system with a tool 520 positioned at least partially within the passageway between the speculum members 135. The tool 520 can be any of a variety of tools for treatment or diagnosis of the tissue accessed by the system 100. In an embodiment, the tool 520 is a tool that is adapted to core into the bone and obtain a sample of the bone. After the tool 520 is used for its intended purpose, the tool 520 can be removed from the passageway between the speculum members 135. The anchor pins 515 can then be removed and the separation between the speculum members 135 can be reduced by operating the handle assembly 105. The system 100 can then be removed by navigating out of the tissue. The generally horizontal upper surfaces 420 of the ribbing is generally perpendicular to the direction of withdrawal to reduce the potential for ejection with soft tissue tensioning. The locking member 205 can be re-attached prior to removal of the system 100. In addition, the handle assembly 105 can be rotated during removal to ease removal.

Although embodiments of various methods and devices are described herein in detail with reference to certain versions, it should be appreciated that other versions, embodiments, methods of use, and combinations thereof are also possible. Therefore the spirit and scope of the snowboard binding should not be limited to the description of the embodiments contained herein.

The invention claimed is:

1. A bone access tool, comprising:
 a handle assembly having a first portion and a second portion that are movable relative to one another;
 a speculum assembly having a central axis coupled to the handle assembly, the speculum assembly comprising:
 (a) a first speculum member;
 (b) a second speculum member movably positioned relative to the first speculum member,
 wherein the first and second speculum members each include a wall having a concave inner surface surrounding the central axis of the speculum assembly, and wherein the walls of the first and second speculum members have a convex outer surface that defines a tapered shape when positioned adjacent one another wherein the tapered shape gradually reduces in size from a proximal rim to a distal edge of the speculum assembly; and
 (c) at least one annular rib extending outwardly from the convex outer surface of each of the first and second speculum members and around the central axis of the speculum assembly, the rib having an upper surface and an inclined lower surface; and
 wherein actuation of the handle assembly causes the first speculum member and second speculum member to spread apart from one another about the central axis so as to retract anatomical tissue and widen a space between the first and second speculum members for deploying a tool through the space between the speculum members.

2. A tool as in claim 1, wherein each of the first and second speculum members are semi-conical in shape and wherein the tapered shape of the speculum assembly is conical when the first and second speculum members are positioned adjacent one another.

3. A tool as in claim 1, wherein the wall of the first and second speculum members meet along a central plane that intersects with the central axis.

4. A tool as in claim 1, wherein the upper surface of each rib is substantially perpendicular relative to the central axis.

5. A tool as in claim 1, wherein the distal edge of the speculum assembly is pointed when the first and second speculum members are positioned adjacent one another.

6. A tool as in claim 1, wherein the concave inner surfaces of the first and second speculum members near a distal edge of the speculum assembly form sides of a hole when the first and second speculum members are in a closed configuration further.

7. A tool as in claim 1, further comprising a speculum cap removably positioned on a proximal rim of the speculum assembly, the speculum cap forming a surface that can be struck by a striking tool to provide a force onto the speculum assembly for driving the speculum assembly into bone.

8. A tool as in claim 7, further comprising a guide wire hole in the speculum cap, the hole being aligned with the central axis instead.

9. A tool as in claim 8, wherein the hole is shaped so as to facilitate insertion of a guide wire into the hole.

10. A tool as in claim 8, wherein the guide wire hole aligns with a second guide wire hole in the distal edge of the speculum assembly along the central axis.

11. A tool as in claim 7, wherein the speculum cap is hinged to the speculum assembly.

12. A tool as in claim 1, wherein the handle assembly is hinged relative to the speculum assembly.

13. A tool as in claim 1, wherein the first and second portions of the handle assembly are elongated arms and wherein the handle assembly is actuated by moving the arms toward one another.

14. A tool as in claim 1, wherein the portions are ratcheted relative to one another.

15. A tool as in claim 1, further comprising a locking member removably coupled to the speculum assembly, wherein the locking member fixes the relative position of the speculum members when coupled thereto.

16. A method of accessing bone, comprising:
 providing an access tool having a handle assembly coupled to a speculum assembly formed of two speculum members that collectively form a substantially conical shape with a pointed distal edge;

navigating the access tool through anatomical tissue so that the pointed distal edge of the speculum assembly is located at a desired anatomical location;

actuating the handle to cause the speculum members to separate from one another to retract anatomical tissue and to form a passageway between the speculum members; and positioning an elongated tool in the passageway and in contact with the anatomical location.

17. A method as in claim 16, further comprising inserting a guide wire at the anatomical location and guiding the speculum assembly over the guide wire.

18. A method as in claim 17, further comprising rotating the speculum assembly and the handle assembly about the guide wire during navigation of the access tool.

19. A method as in claim 16, further comprising removing a locking member from the tool to permit actuation of the handle.

20. A method as in claim 16, wherein the anatomical location is the iliac crest.

21. A bone access tool, comprising:

a handle assembly having a first handle portion with a proximal end, and middle region and a distal end and a second handle portion with a proximal end, a middle region and a distal end, wherein the first portion and second portion are rotatably coupled to one another near their middle regions by a pivot assembly and movable relative to one another around the pivot assembly;

a speculum assembly coupled to the handle assembly distal of the pivot assembly, the speculum assembly comprising:

(a) a first speculum member having a proximal rim and a distal edge, wherein a portion of the proximal rim is coupled to the distal end of the first handle portion;

(b) a second speculum member having a proximal rim and a distal edge, wherein a portion of the proximal rim is coupled to the distal end of the second handle portion, wherein the second speculum member is movably positioned relative to the first speculum member, wherein the first and second speculum members each comprise a concave inner surface, and wherein the first and second speculum members each comprise a convex outer surface that define a tapered shape when positioned adjacent one another, the tapered shape gradually reducing in size from the proximal rims to the distal edges of the first and second speculum members; and (c) at least one rib extending outwardly from each of the first and second speculum members, the rib having an upper surface and an inclined lower surface, wherein actuation of the handle assembly around the pivot assembly causes the proximal rim and the distal edge of the first speculum member to spread apart from the proximal rim and the distal edge of the second speculum member so as to retract anatomical tissue and widen a space between the speculum members.

* * * * *